United States Patent [19]
Reed

[11] Patent Number: 4,759,748
[45] Date of Patent: Jul. 26, 1988

[54] GUIDING CATHETER

[75] Inventor: James P. Reed, Redwood City, Calif.

[73] Assignee: Raychem Corporation, Menlo Park, Calif.

[21] Appl. No.: 909,974

[22] Filed: Sep. 22, 1986

Related U.S. Application Data

[63] Continuation-in-part of Ser. No. 880,107, Jun. 30, 1986, abandoned, which is a continuation of Ser. No. 778,578, Sep. 20, 1985, abandoned.

[51] Int. Cl.⁴ .......................................... A61M 25/00
[52] U.S. Cl. ..................................... 604/95; 604/104; 128/348.1
[58] Field of Search ............................... 604/95–103; 128/325, 343, 344, 348.1

[56] References Cited

U.S. PATENT DOCUMENTS

| | | | |
|---|---|---|---|
| 2,610,626 | 9/1952 | Edwards | 604/101 |
| 2,650,592 | 9/1953 | Borda | 128/278 |
| 2,845,930 | 8/1958 | Brown | 128/748 X |
| 3,050,066 | 8/1962 | Koehn | 604/96 |
| 3,065,750 | 11/1962 | Mandell | 604/96 |
| 3,105,492 | 10/1963 | Jeckel | 128/334 R |
| 3,168,092 | 2/1965 | Silverman | 128/1.2 |
| 3,276,448 | 10/1966 | Kronenthal | 128/334 R |
| 3,316,557 | 5/1967 | Liebig | 128/334 R |
| 3,428,046 | 2/1969 | Remer et al. | 604/265 |
| 3,509,883 | 5/1970 | Dibelius | 128/343 |
| 3,562,352 | 2/1971 | Nyilas | 260/824 |
| 3,568,659 | 3/1971 | Karnegis | 128/1 D |
| 3,588,920 | 6/1971 | Wesolowski | 128/334 R |
| 3,592,183 | 7/1971 | Watkins et al. | 128/1 D |
| 3,726,281 | 4/1973 | Norton et al. | 604/96 |
| 3,773,034 | 11/1973 | Burns et al. | 604/95 X |
| 3,788,318 | 1/1974 | Kim | 128/343 X |
| 3,996,938 | 12/1976 | Clark | 128/348.1 |

(List continued on next page.)

FOREIGN PATENT DOCUMENTS

| | | |
|---|---|---|
| 1095457 | 11/1959 | Fed. Rep. of Germany . |
| 51-72194 | 6/1976 | Japan . |
| 53-139390 | 12/1978 | Japan . |
| 54-48989 | 4/1979 | Japan . |
| 55-166148 | 12/1980 | Japan . |
| 56-40423 | 5/1981 | Japan . |
| 58-7263 | 1/1983 | Japan . |
| WO81/02110 | 8/1981 | PCT Int'l Appl. . |
| WO83/03732 | 11/1983 | PCT Int'l Appl. . |
| WO84/01513 | 4/1984 | PCT Int'l Appl. . |
| 1205743 | 9/1970 | United Kingdom . |
| 1566674 | 5/1980 | United Kingdom . |
| 2150837 | 7/1985 | United Kingdom . |
| 1060190 | 12/1983 | U.S.S.R. . |

OTHER PUBLICATIONS

Caponigro, D. A., "Prosthetic Stut", Ser. No. 663,013, filed 10/19/84.
McAuley et al., "Advances in Guidewire Technology", Am. J. Cardial, 1984: 53:940–960.
Lee et al., "Potential Complications of Coronary Laser Angioplasty", Am. Heart J., 12/84, pp. 1157–1159.
Wilson et al., "Percutaneous Transluminal Angioplasty", Surgical Clinics of N. America, vol. 64, No. 1, 2/84, pp. 121–150.

Primary Examiner—Dalton L. Truluck
Attorney, Agent, or Firm—Edith A. Rice; Herbert G. Burkard

[57] ABSTRACT

A guiding catheter has incorporated toward its distal end, a flexible member capable of non-uniform elongation to cause the distal end portion to bend and straighten as desired so that it can be maneuvered through and accurately positioned in a tortuous, non-linear conduit containing branches, for example blood vessels. The flexible member comprises interconnected, and preferably braided, filaments with gaps between the filaments. The member has a first configuration that is axially lengthened and a second configuration that is axially shortened. Means are provided to move the member between its first and second configurations. Biasing means are provided to restrict axial lengthening along one side of the flexible member resulting in bending of the catheter tip.

19 Claims, 2 Drawing Sheets

U.S. PATENT DOCUMENTS

| | | |
|---|---|---|
| 4,022,216 | 5/1977 | Stevens .................. 604/101 |
| 4,182,339 | 1/1980 | Hardy, Jr. .............. 128/334 R |
| 4,190,909 | 3/1980 | Ablaza .................. 128/334 RX |
| 4,245,624 | 1/1981 | Komiya .................. 128/4 |
| 4,307,772 | 12/1981 | Evans .................. 128/344 |
| 4,315,512 | 2/1982 | Fogerty .................. 128/344 |
| 4,327,720 | 5/1982 | Bronson et al. .......... 128/207.15 |
| 4,368,739 | 1/1983 | Nelson, Jr. .............. 604/54 |
| 4,413,989 | 8/1983 | Schjeldahl .............. 604/96 |
| 4,434,797 | 3/1984 | Silander .................. 128/343 |
| 4,437,857 | 3/1984 | Goldstein et al. .......... 604/53 |
| 4,448,195 | 5/1984 | LeVeen .................. 128/344 |
| 4,553,545 | 11/1985 | Maass et al. ............ 128/341 |
| 4,572,186 | 2/1986 | Gould .................... 128/341 |
| 4,586,923 | 5/1986 | Gould et al. ............ 604/95 |
| 4,650,466 | 3/1987 | Luther .................. 604/95 |

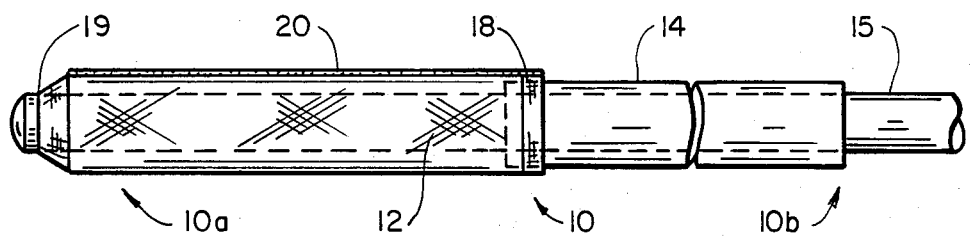
FIG_1A
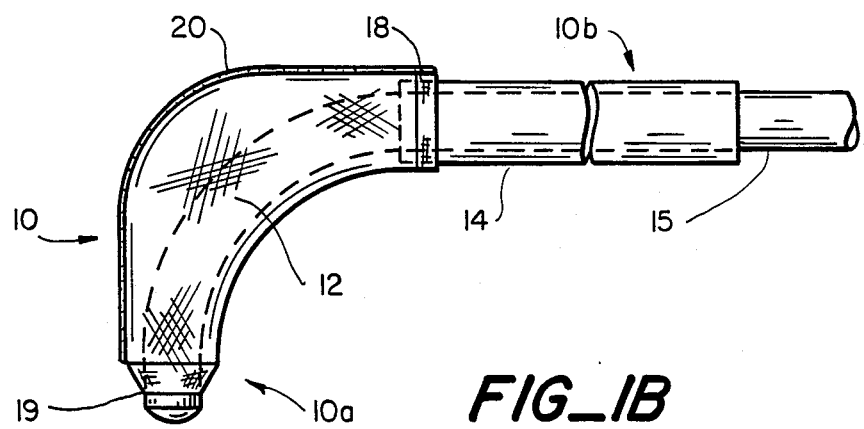
FIG_1B

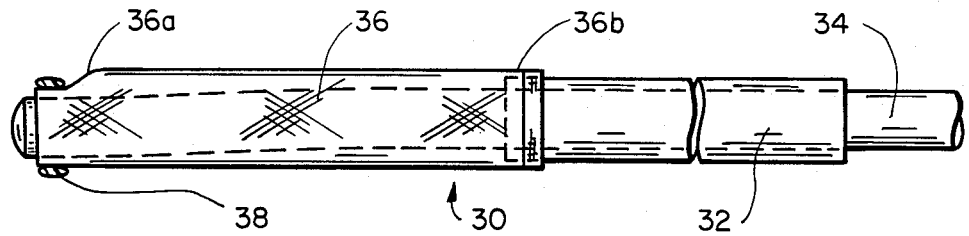
FIG_2
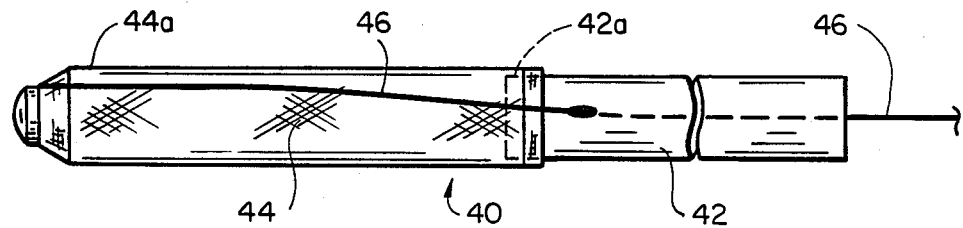
FIG_3
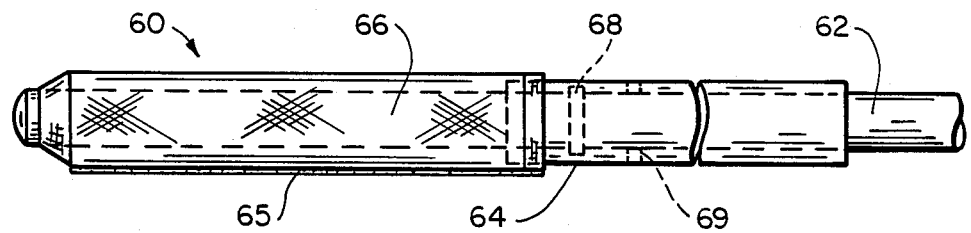
FIG_4

A
GUIDING CATHETER

This application is a continuation-in-part of application Ser. No. 880,107 filed June 30, 1986 which in turn is a continuation of application Ser. No. 778,575, filed Sept. 20, 1985, both now abandoned, the disclosure of which is incorporated herein by reference.

BACKGROUND OF THE INVENTION

This invention is directed to a guiding catheter for negotiating a tortuous non-linear conduit and to a method for its use.

In many medical procedures, such as percutaneous transluminal angioplasty, it is necessary to advance a catheter through a narrow tortuous blood vessel without damaging the endothelium. A variety of systems are used, such as guide wires, for example, see U.S. Pat. No. 4,436,017, guiding catheters, for example, see U.S. Pat. No. 3,773,034, and everting catheters, for example, see U.S. Pat. No. 4,437,857. A difficulty with commonly used guiding systems is that the procedure is time consuming and requires great skill on the part of the surgeon. Also many systems require the use of a large number of pre-bent guiding tips for accommodating different changes in the path of the vascular system.

The guiding, i.e. steerable, catheter disclosed in U.S. Pat. No. 3,773,034 has at its distal end a steerable tip formed of a flexible, thin, stretchable and contractible material. As the pressure of fluid within the distal end is varied, the steerable tip axially elongates or contracts. One longitudinally extending portion of the tip is restrained from stretching so that an increase in pressure on the fluid in the catheter results in bending of the steerable tip. The restraint may be the walls of the blood vessel or other channel in which the catheter is being inserted or an axially restraining means in the wall of the catheter tip. One disadvantage of this catheter is that if there is a constriction, e.g. caused by the blood vessel walls or improper positioning of the catheter, increased fluid pressure may not cause the desired bending. The degree of bending will be unknown by the person inserting the catheter who will be able to note only the increase in fluid pressure.

There is a need for a device for accessing remote regions of the vascular system without problems associated with current devices.

SUMMARY OF THE INVENTION

The present invention is directed to devices satisfying these needs, as well as novel methods for using these devices. A guiding catheter has incorporated toward its distal end, a flexible member capable of non-uniform elongation to cause the distal end portion to bend and straighten as desired so that it can be maneuvered through and accurately positioned in a tortuous, non-linear conduit containing branches, for example blood vessels. The flexible member comprises interconnected, and preferably braided, filaments with gaps between the filaments. The member has a first configuration that is axially lengthened and a second configuration that is axially shortened. Means are provided to move the member between its first and second configurations. Biasing means are provided to restrict axial lengthening along one side of the flexible member resulting in bending of the catheter tip.

One aspect of this invention comprises a guiding catheter for negotiating a tortuous, non-linear conduit, the catheter having a longitudinal axis, a proximal end, and a distal end, the catheter comprising:
  (a) an elongated tubular anchor member having a distal portion and a proximal portion;
  (b) an elongated activating member having a distal portion and a proximal portion which extends beyond the proximal portion of the anchor member; and
  (c) a flexible member comprising interconnected filaments attached to the outer surface of the distal portion of the anchor member at a first location and also attached to a distal portion of the activating member at a second location, the first and second locations being axially spaced apart from each other, both the anchor member and the activating member being substantially rigid in compression where attached to the flexible member, the flexible member having a first configuration that is axially lengthened and a second configuration that is axially shortened, said flexible member also comprising means for preventing axial lengthening of the flexible member along one side thereof, wherein the flexible member in one of said configurations is bent such that the distal end of the catheter is transverse to the longitudinal axis of the catheter, and in the other said configuration is substantially straight;

and wherein relative axial movement between the anchor member and the activating member reversibly moves the flexible member from one configuration to the other configuration for varying the amount the distal end of the catheter is transverse to the longitudinal axis of the catheter.

Another aspect of this invention comprises a method for accessing a relatively inaccessible region of a tortuous non-linear conduit comprising the steps of:
  (a) entering the conduit with a guiding catheter having a longitudinal axis, a proximal end, and a distal end, the distal end being placed first into the conduit, the catheter comprising:
    (i) an elongated tubular anchor member having a distal portion and a proximal portion;
    (ii) an elongated activating member having a distal portion and a proximal portion which extends beyond the proximal portion of the anchor member; and
    (iii) a flexible member comprising interconnected filaments attached to a distal portion of the anchor member at a first location and also attached to a distal portion of the activating member at a second location, the first and second locations being axially spaced apart from each other, both the anchor member and the activating member being substantially rigid in compression where attached to the flexible member, the flexible member having a first configuration that is axially lengthened and a second configuration that is axially shortened, said flexible member also comprising means for preventing axial lengthening of the flexible member along one side thereof, wherein the flexible member in one of said configurations is bent such that the distal end of the catheter is transverse to the longitudinal axis of the catheter and in the other of said configurations is substantially straight, and wherein the relative axial movement between the anchor member and the activating member reversibly moves the flexible member from one configuration to the other configuration for varying the amount the distal end of the catheter is transverse to the longitudinal axis of the catheter; and (b) moving the catheter through the conduit toward the inaccessible region while causing relative axial movement between the anchor and activating members for varying the amount the distal end of the catheter is transverse to the longitudinal axis of the catheter for accommodating non-linearity of the conduit.

The flexible member of interconnected, and preferably braided, filaments with gaps between the filaments has a first configuration that is axially lengthened and a second configuration that is axially shortened. Means are provided to restrict axial lengthening (or shortening) along one side of the member so that in either the first or the second configuration, the flexible member is bent, that is the distal end of the catheter is transverse to the longitudinal axis of the catheter. There are two elongated members, a first elongated anchor member attached to the flexible member at a first location of the flexible member and a second elongated activating member attached to the flexible member at a second location of the flexible member. The second location is axially spaced apart from the first location. Relative axial movement between the first and second members moves the flexible member from one of the configurations to the other configuration.

Both members can be accessed from the same end of the device, i.e. both members extend from the proximal portion of the device to the flexible member. Generally the activating members extends from the proximal portion of the device to the distal portion of the flexible member and the anchor member extends to the proximal portion of the flexible member.

The catheter can be rotated by rotating at least the anchor member thereby facilitating manipulation of the catheter along the tortuous conduit and into branch conduits. Thus, the catheter bending is not unidirectional but can occur in any desired direction.

In a preferred embodiment, the flexible member is attached to the outer surface of the anchor member and to the outer surface of the distal portion of the activating member. The flexible member is preferably biased so that it is in its axially lengthened configuration in its at rest state. By "at rest state" is meant the configuration of the member when no force is applied thereto. Relative axial movement between the inner and outer members so that the points at which the flexible member is attached to the anchor and activating members become closer together, results in bending of member by non-uniform axial lengthening of the flexible member. The amount the distal end is bent can be controlled by varying the relative position of the anchor members.

A stop can be provided for limiting the amount the flexible member expands and therefore limiting the degree of bending of the catheter's distal end. The catheter can be provided with a second bending flexible member if desired. The two bendable members can be concentric or can be axially spaced apart. If axially spaced apart, the distal end can assume a double bend or other complex configuration to enable it to traverse complex tortuous conduits and branches.

The region between the inner activating member and the outer anchor member can be used for carrying fluids into a patient or from a patient. The inner member can be solid in cross-section, or can be tubular, and if tubular, the lumen of the inner member can be used for carrying fluids to a patient or from a patient.

BRIEF DESCRIPTION OF THE DRAWINGS

These and other features, aspects, and advantages of the present invention will become better understood from the following description, appended claims, and accompanying drawings where:

FIG. 1A is a side elevation view, partly in section, of a guiding catheter according to the present invention in its substantially straight configuration;

FIG. 1B is a side elevation view, partly in section, of the guiding catheter of FIG. 1A in its bent configuration;

FIG. 2 is a side elevation view, partly in section, of another guiding catheter according to the present invention.

FIG. 3 is a side elevation view, partly in section, of another guiding catheter according to the present invention.

FIG. 4 is a side elevation view, partly in section, of another device according to the present invention in its substantially straight configuration including stop means for limiting the degree of bending of the flexible member.

DETAILED DESCRIPTION OF THE INVENTION

As shown in FIGS. 1A and 1B, a guiding catheter 10 according to the present invention comprises a flexible member 12 of interconnected filaments with gaps therebetween. The catheter 10 has a distal portion 10a and a proximal portion 10b. As shown in FIG. 1A, the flexible member 12 has a first configuration that is substantially straight and axially lengthened, and as shown in FIG. 1B, has a second configuration that is bent and axially shortened.

The flexible member 12 is moved from one configuration to the other configuration by relative axial movement of anchoring member 14 and activating member 15. The flexible member 12 is attached to the anchoring member 14 and activating member 15 at locations 18 and 19 respectively, the two locations being axially spaced apart from each other. Both anchor members 14 and 15 lead into the flexible member 12 from the same direction, i.e. from the proximal portion 10b of the device. Thus the anchoring member 14 is connected to the proximal portion of the flexible member 12 and the activating member 15 is connected to the distal portion of the flexible member 12. The activating member 15 extends from the proximal portion of the anchor member through the distal portion of the anchor member 14.

Relative axial movement between the anchor member 14 and activating member 15 is produced by pulling on activating member 15 while restraining anchor member 14 causing the first 18 and second 19 locations to move closer to each other, resulting in the flexible member 12 moving from its axially lengthened configurations to its axially shortened configuration. Flexible member 12 is provided with a bonding means illustrated as adhesive strip 20 which bonds the interconnecting filaments and prevents axial shortening of the member along the adhesive strip. This results in a moment being produced along the edge of the flexible member causing it to bend as shown in FIG. 1B. Similarly, once the flexible member 12 is in the configuration shown in FIG. 1B, relative axial movement between anchor member 14 and activating member 15 in the opposite direction causes the flexible member 12 to move back to its axially lengthened, substantially straight configuration shown in FIG. 1A.

It is to be understood that relative axial movement results in the change in configuration. For example, to move the flexible member from its axially lengthened, substantially straight configuration shown in FIG. 1A to the axially shortened, bent configuration shown in FIG. 1B, any or all of the following steps can be taken:
  (a) Pull (tensile force) on the proximal portion of the activating member 15 with concurrent push (compressive force) on the proximal portion of the anchoring member 14; or
  (b) Push (compressive force) on the distal portion 15b of the activating member 15 with concurrent pull (tensile force) on the proximal end of the anchor member 14.

In this application it is to be understood that when force on the activating member is referred to, the concurrent opposite force is applied to the anchor member. Sufficient compressive force can be applied e.g. to the anchor member, by restraining it from motion while the activating member is pulled from its axial end.

Typically, the anchor member 14 is tubular and the activating member 15 is within the lumen of the anchor member 14 for at least part of its length. The tubular anchor member can be circular in cross-section, or can have other cross-sections such as oval, star shaped, or other irregular pattern. As shown in FIGS. 1A and FIGS. 1B, the activating member 15 can also be tubular. As shown in FIG. 3, the activating members can be solid in cross-section.

The anchor and activating members 14 and 15 are formed from a material sufficiently flexible to navigate tortuous paths yet sufficiently rigid in compression and/or tension so that the anchor and activating members are capable, without buckling, of causing the flexible member to move from one configuration to the other. In some embodiments, e.g. where the flexible member is biased (as discussed below) to automatically revert to its axially lengthened configuration, the activating member need not be rigid under compression.

The flexible member 12 is attached or bonded to the anchor members 14 and 15 by any of a variety of techniques, including welding, fusing, heat shrink tubing, or use of an adhesive such as an epoxy based adhesive.

The materials used for the anchor and activating members should be biocompatible materials. By the term "biocompatible" there is meant a material that is non-toxic and noncarcinogenic. Exemplary of materials that can be used are metals such as titanium, medical grade stainless steel, and platinum. Suitable polymeric materials include polyethylene; acrylics; Teflon (Trademark) polytetrafluoroethylene (PTFE); polyesters such as those sold under the trademark Dacron; polysulfones; polyurethane elastomers; silicones; polyolefin elastomers; medical grad epoxy resins; synthetic and natural rubbers; cellulosic materials such as cellulose acetate, cellulose acetate butyrate, and ethyl cellulose; and nylon.

The flexible member 12 is formed of interconnected filaments, preferably formed as a braid, i.e. comprises three or more component strands forming a regular diagonal pattern down its length. The resulting structure resembles a "Chinese finger handcuff" device where a series of interwoven fibers are arranged helically and configured into a tubular shape. Each fiber is capable of simultaneous angular rotation.

Substantially any fiber can be used for the flexible member 12. For medical applications, preferably the flexible member 12 is made from biocompatible materials. Some examples of suitable materials are thermoplastic polyester, polyethylene, thermoplastic soft segment polyurethane, polymethylmethacrylate, polytetrafluorotheylene, silicone polymers, and elastomeric polyurethane polymers. For applications where the device 10 is used in contact with blood, preferably the materials used for the anchor members and the flexible member are polymeric substances that do not promote thrombosis or blood clotting on their surfaces, i.e. the materials are non-thrombogenic.

The flexible member 12 includes means for preventing a longitudinal portion of the flexible member from axially lengthening. For example, the flexible member 12 can include an elongated strip 20 of adhesive along its length for interconnecting the filaments and preventing them from relative movement. Because of the strip 20 of material, the flexible member cannot shorten in the region of the strip 20. Upon relative axial movement between the anchor member 14 and the activating member 15, only a portion of the flexible member 12 shortens, with a resultant bending moment on the distal portion. As shown in FIGS. 1A and 1B, this bending moment results in the flexible member 12 and the distal portion 10a of the catheter 10 being bent so that the distal portion of the catheter is transverse to the longitudinal axis. For this to occur, it is necessary that at least the distal portion of the activating member 15 be sufficiently flexible that it can bend. In addition the anchoring member 14 needs to be sufficiently rigid in compression that when the activating member 15 is pulled relative to the anchoring member 14, the flexible member 12 shortens rather than the anchoring member 14 buckling. Shortening of the flexible member 12 is reversible. For this to occur, it is necessary that the activating member 15 be sufficiently rigid in compression that it does not buckle when the activating member 15 is moved to move the flexible member 12 to its axially lengthened configuration. Thus relative axial movement between the anchoring member 14 and the activating member 15 can reversibly move the flexible member 12 from one configuration to the other configuration for varying the amount the distal end 10a of the catheter 10 is transverse to the longitudinal axis. Other means for preventing lengthening of the flexible member along one side thereof. Any bonding means such as adhesive can be used. A strip of non-stretchable material can be secured to the flexible member, e.g. by adhesion, sewing fusion or the like or incorporated into the flexible member, e.g. by interweaving non-stretchable warp filaments along one edge of the flexible member. The warp filaments can extend beyond the flexible member and act as the activating member (providing the flexible member is biased in its axially lengthened configuration).

Any of the components of a catheter according to the present invention can be made self-lubricating, by incorporating therein a finely divided solid lubricant such as molybdenum disulfide, graphite, tungsten disulfide, molybdenum selenide, or titanium disulfide. Also any of the components can be coated with a lubricant such as PTFE. These lubricating materials greatly facilitate the displacement of the catheter 10 over a mucous surface.

In a catheter according to the present invention, there can be a flexible impervious membrane, preferably in the shape of a band, on the flexible member, the band being substantially impervious to particular liquids and/or gases. In this version of the invention the band, e.g. of natural or synthetic rubber, can be used for preventing flow through a vessel.

A catheter according to the present invention can comprise two or more bendable, flexible members, positioned at the distal end of the catheter.

The flexible member can be biased into either a lengthened or shortened configuration, by, for example, orienting and heat-setting or annealing the braided filaments. By "biased" is meant that the flexible member will at rest be in its first (or second) configuration and will revert to that configuration from any other configuration unless restrained from doing so.

An advantage of the catheter 10 is that the bend at the tip is infinitely variable so that the catheter 10 can be used for navigating substantially all of the turns in a blood vessel system and accommodate differences in the patient's anatomy. Further, the catheter 10 can readily be rotated to bend in any direction and thus can be directed to focus on the entrance of a branch conduit, e.g. the coronary artery from the aorta. This ability to rotate the catheter and then bend the flexible member in the desired direction and to the desired extent is generally unattainable by prior art devices.

FIG. 2 shows another catheter device 30. The catheter 30 includes an outer tubular anchor member 32, an inner tubular anchor member 34 in the lumen of the outer member 32, and a flexible member 36 attached at its distal end 36a by heat shrink tubing 38 to the inner anchor member 34 and attached at its proximal end 36b by adhesive to the outer tubular member 32. As shown in FIG. 2, the inner anchor member 34 is coaxial with the flexible member 36. At the proximal end 36b of the flexible member, the inner anchor member 34 is at about the longitudinal center line of the flexible member 36. However, at the distal end 36a of the flexible member 36, the inner anchor member 34 is offset from the longitudinal center line of the flexible member 36. Thus in the region of the flexible member, the longitudinal axis of the inner tubular member 34 is skewed or transverse relative to the longitudinal center line of the flexible member 36. Because of this skewed configuration, when the inner tubular member 34 is pulled, the flexible member 36 develops a bend and can have the same bent configuration of the catheter 10 shown in FIG. 1B.

FIG. 3 shows another catheter device 40. The catheter 40 includes a tubular anchor member 42 with a flexible member 44 attached at its distal end 42a. Activating member 46 is attached at a point at the distal end 44a of flexible member 44. The activating member 46 is a solid rod which in this embodiment passes outside flexible member 44 and into the lumen of anchoring member 42. It is to be understood that the activating member could be inside the tubular flexible member or woven into it. When activating member 46 is pulled, its point attachment to flexible member 44 causes the flexible member to bend. The flexible member 44 can revert to its substantially straight, axially lengthened, substantially straight configuration by pushing an activating member 46 or the filaments of flexible member 44 can be biased such when the pulling force applied to activating member 46 is removed, the flexible member 44 automatically reverts to its substantially straight configuration.

In some applications, it is desirable to limit the amount the flexible member can bend. For example, if the flexible member is placed into a small diameter blood vessel, it is desirable that the amount that the flexible member can be expanded be limited so that the operator of the device does not inadvertently overexpand the flexible member thereby damaging tissue. The catheter 60 shown in FIG. 4 is particularly adapted for this purpose.

In FIG. 4, the activating member 62 of catheter 60 can be provided with an annular projection 68 that can engage a cooperating radially outwardly projecting ring 69 on the interior of the anchoring member 64. These interengaging stops limit the amount the activating member 62 can be pulled axially, thereby limiting the amount of expansion of the flexible member 66. Flexible member 66 is provided with a strip of adhesive 65 which prevents axial shortening of the flexible member 66 along the strip causing bending of the flexible member 66. The interengaging stops 68 and 69 thus limit the amount of bending of catheter 60. If desired, the stop can be positioned at the proximal end of the device limiting the amount the activating member can move with respect to the anchoring member.

EXAMPLE 1

Guiding Catheter

A guiding catheter 10 as shown in FIGS. 1A and 1B comprises an outer tubular anchoring member 14 which is 50 inches long with an outer diameter of from 80 to 120 mil and an inner diameter of from 70 to 90 mil. The inner tubular activating member 15 is 60 inches long, has an outer diameter of from 68 to 80 mils, and an inner diameter of from 50 to 62 mils. Both tubes can be made of polytetrafluoroethylene or polyethylene. The inner diameter of the outer tube is of course greater than the outer diameter of the inner tube. The flexible member 20 is formed from polyethylene filaments having a diameter of from 6 to 10 mil. The flexible member 20 in its axially lengthened, substantially straight configuration has an outer diameter of 120 mil. The flexible member is bonded to the inner and outer tubes with medical grade epoxy.

Although the present invention has been described in considerable detail with reference to certain preferred versions are possible. Therefore the spirit and scope of the appended claims should not be limited to the description of the preferred versions.

What is claimed is:

1. A guiding catheter for negotiating a tortuous, nonlinear conduit, the catheter having a longitudinal axis, a proximal end, and a distal end, the catheter comprising:
   (a) an elongated anchor member having a distal portion and a proximal portion;
   (b) an elongated activating member having a distal portion and a proximal portion which extends beyond the proximal portion of the anchor member; and
   (c) a flexible member comprising interconnected filaments attached to the outer surface of the distal portion of the anchor member at a first location and also attached to a distal portion of the activating member at a second location, the first and second locations being axially spaced apart from each other, said anchor member being substantially rigid in compression where attached to the flexible member, the flexible member having a first configuration that is radially contracted and axially lengthened and a second configuration that is radially expanded and axially shortened, said flexible member also comprising means for preventing axial lengthening of the flexible member along one side thereof, wherein the flexible member in the radially expanded configuration is bent such that the distal end of the catheter is transverse to the longitudinal axis of the catheter, and in the radially contracted configuration is substantially straight; and wherein relative axial movement between the anchor member and the activating member reversibily moves the flexible member from one configuration to the other configuration for varying the amount the distal end of the catheter is transverse to the longitudinal axis of the catheter.

2. The device of claim 1 in which the filaments are braided.

3. The device of claim 1 in which the anchor member is tubular.

4. The device of claim 3 in which the activating member is at least partially exterior of the first anchor member.

5. The device of claim 4 in which the activating member is at least partially in the lumen of the anchor member.

6. The device of claim 5 in which the anchor and activating members are tubular and coaxial.

7. The device of claim 6 in which the flexible member is coaxial with the anchor and activating members and is attached to the exterior of the anchor member and the exterior of the activating member.

8. The device of claim 7 in which the flexible member has a distal and a proximal portion and the distal portion is attached to the distal portion of the activating member and the proximal portion is attached to the distal portion of the anchor member.

9. The device of claim 1 in which the activating member is a rod.

10. The device of claim 1 including stop means for limiting the degree of bending of the flexible member, 11. A method for accessing a relatively inaccessible region of a tortuous non-linear conduit comprising the steps of:
  (a) entering the conduit with a guiding catheter having a longitudinal axis, a proximal end, and a distal end, the distal end being placed first into the conduit, the catheter comprising:
    (i) an elongated tubular anchor member;
    (ii) an elongated activating member, a distal portion and a proximal portion which extends beyond the proximal portion of the anchor member; and
    (iii) a flexible member comprising interconnected filaments attached to a distal portion of the anchor member at a first location and also attached to a distal portion of the activating member at a second location, the first and second locations being axially spaced apart from each other, said anchor member being substantially rigid in compression where attached to the flexible member, the flexible member having a first configuration that is radially contracted and axially lengthened and a second configuration that is radially expanded and axially shortened, said flexible member also comprising means for preventing axial lengthening of the flexible member along one side thereof, wherein the flexible member in the radially expanded configuration is bent such that the distal end of the catheter is transverse to the longitudinal axis of the catheter and in the radially contracted configuration is substantially straight, and wherein the relative axial movement between the anchor member and the activating member reversibly moves the flexible member from one configuration to the other configuration for varying the amount the distal end of the catheter is transverse to the longitudinal axis of the catheter; and
  (b) moving the catheter through the conduit toward the inaccessible region while causing relative axial movement between the inner and outer members for varying the amount the distal end of the catheter is transverse to the longitudinal axis of the catheter for accomodating non-linearity of the conduit.

12. A guiding catheter for negotiating a tortuous, nonlinear conduit, the catheter having a longitudinal axis, a proximal end, and a distal end, the catheter comprising:
  (a) an elongated anchor member having a distal portion and a proximal portion;
  (b) an elongated activating member having a distal portion and a proximal portion which extends beyond the proximal portion of the anchor member; and
  (c) a flexible member comprising interconnected filaments attached to the outer surface of the distal portion of the anchor member at a first location and also attached to a distal portion of the activating member at a second location in a manner such that the point of attachment is offset from the center line of said flexible member, the first and second locations being axially spaced apart from each other, said anchor member being substantially rigid in compression where attached to the flexible member, the flexible member having a first configuration that is radially contracted and axially lengthened and a second configuration that is radially expanded and axially shortened, wherein the flexible member in the radially expanded configuration is bent such that the distal end of the cathether is transverse to the longitudinal axis of the catheter, and in the radially contracted configuration is substantially straight; and wherein relative axial movement between the anchor member and the activating member reversibly moves the flexible member from one configuration to the other configuration for varying the amount the distal end of the catheter is transverse to the longitudinal axis of the catheter.

13. The device of claim 12 in which the filaments are braided.

14. The device of claim 12 in which the anchor member is tubular.

15. The device of claim 14 in which the activating member is at least partially exterior of the first anchor member.

16. The device of claim 15 in which the activating member is at least partially in the lumen of the anchor member.

17. The device of claim 12 in which the activating member is a rod.

18. The device of claim 12 including stop means for limiting the degree of bending of the flexible member.

19. A method for accessing a relatively inaccessible region of a tortuous non-linear conduit comprising the steps of:

(a) entering the conduit with a guiding catheter having a longitudinal axis, a proximal end, and a distal end, the distal end being placed first into the conduit, the catheter comprising:
  (i) an elongated tubular anchor member;
  (ii) an elongated activating member, a distal portion and a proximal portion which extends beyond the proximal portion of the anchor member; and
  (iii) a flexible member comprising interconnected filaments attached to a distal portion of the anchor member at a first location and also attached to a distal portion of the activating member at a second location in a manner such that the point of attachment is offset from the center line of said flexible member, the first and second locations being axially spaced apart from each other, said anchor member being substantially rigid in compression where attached to the flexible member, the flexible member having a first configuration that is radially contracted and axially lengthened and a second configuration that is radially expanded and axially shortened, wherein the flexible mmeber in the radially expanded configuration is bent such that the distal end of the catheter is transverse to the longitudinal axis of the catheter and in the radial contracted configuration is substantially straight,
  and wherein the relative axial movement between the anchor member and the activating member reversibly moves the flexible member from one configuration to the other configuration for varying the amount the distal end of the catheter is transverse to the longitudinal axis of the catheter; and
(b) moving the catheter through the conduit toward the inaccessable region while causing relative axial movement between the inner and outer members for varying the amount the distal end of the catheter is transverse to the longitudinal axis of the catheter for accomodating non-linearity of the conduit.

* * * * *